United States Patent [19]

Tamulis

[11] 4,413,628
[45] Nov. 8, 1983

[54] PH MONITOR ELECTRODE ELECTROLYTE CARTRIDGE

[76] Inventor: Walter G. Tamulis, 239B Twin Lakes Rd., North Branford, Conn. 06471

[21] Appl. No.: 208,143

[22] Filed: Nov. 19, 1980

[51] Int. Cl.³ .............................................. A61B 5/00
[52] U.S. Cl. .................................... 128/635; 204/403; 204/409
[58] Field of Search .............................. 128/635, 641; 204/195 B, 195 G, 195 L, 195 M, 195 P

[56] References Cited

U.S. PATENT DOCUMENTS

| | | | |
|---|---|---|---|
| 3,211,638 | 10/1965 | Holvorsen | 204/195 P |
| 3,942,517 | 3/1976 | Bowles et al. | 128/641 |
| 4,274,418 | 6/1981 | Vesterager et al. | 128/635 |

*Primary Examiner*—Lee S. Cohen
*Attorney, Agent, or Firm*—Joseph E. Funk

[57] ABSTRACT

A disposable pH monitor electrode electrolyte cartridge is disclosed that is quickly and easily attached to a probe base to make up a pH monitor electrode assembly. The cartridge contains an electrolyte confined by membranes that are pierced by a probe tip protruding from the probe base when the cartridge is assembled thereto.

4 Claims, 4 Drawing Figures

PH MONITOR ELECTRODE ELECTROLYTE CARTRIDGE

FIELD OF THE INVENTION

This invention relates to electrode cell assemblies for the determination of ion concentrations in body fluids.

BACKGROUND OF THE ART

Electrode cell assemblies for the determination of ion concentrations are known in the art and said electrode cell assenblies comprise a measuring electrode, which is immersed into the solution in which the ion concentration shall be determined as well as a reference electrode, which is immersed in an electrolyte solution. The electrical conductivity between the solution in which the ion concentration shall be deternined and the electrolyte solution in which the reference electrode is immersed, is generally provided by a bridge solution, i.e., a conduit which is filled with an electrolyte, e.g., the solution into which the reference electrode is immersed, and wherein the end of said conduit is provided with a membrane so that said conduit can be immersed into the solution in which the ion concentration has to be determined, which membrane or diaphragm is an impermeable barrier which prevents the bridge solution (electrolyte solution) from flowing out. The measuring electrode has an ion sensitive member which is immersed into the solution in which the ion concentration shall be determined and said measuring electrode, furthermore, has a buffer solution filling into which the internal reference electrode of said measuring electrode is immersed. The internal reference electrode of the measuring electrode and also the reference electrode are connected with a conductor and the other ends of those conductors are connected via the recording device so that the EMF is recorded by said recording device. The measuring electrode has an ion sensitive member which is immersed into the solution wherein the ion concentration has to be determined and said measuring electrode can, e.g., be one of the well known glass electrodes in which the ion sensitive member is a glass membrane. Electrode cell assemblies in which the measuring electrode is a glass electrode are frequently used for the determination of the pH-value of the solutions.

Furthermore, it is well known in the art to determine the ion concentration in body fluids, e.g., in blood, by using an electrode cell assembly as described above and immersing the measuring electrode into a sample of the body fluid. The ion concentration of said body fluid is then recorded with the calibrated recording device. Said method, for instance, can be applied for the determination of the pH-valve of blood samples of a person by taking at certain intervals blood samples from said person and determining the pH-valve of said blood samples by using a glass electrode as the measuring electrode.

The pH-valve of the blood makes it possible to estimate the carbon dioxide concentration in the blood, i.e., if the the pH-value of the blood is sinking, this means that the carbon dioxide concentration in the blood is increasing. The increased carbon dioxide concentration in the blood shows that the organs of the living being are not provided with sufficient oxygen and this may be toxic or harmful for the organs, especially for the brain. It would be very advantageous if narcotized persons and persons who are submitted to an intensive medical treatment were continuously observed with regard to the pH-value of their blood so that by such a continuous determination of the pH-value, any increase of the $CO_2$-content in the organism could be noticed immediately. Specially important, however, would be such a continuous investigation if it were possible during pregnancy when any insufficient oxygen supply for the organism of the infant may occur and, furthermore, in the course of a delivery, i.e., during the period of the opening of the cervix and the extrusion of the infant. It is well known that an increase of the carbon dioxide concentration in the blood of the infant, which, e.g., might occur because of a compression of the umbilical cord during the delivery, may cause a permanent damage of the brain of the infant (cerebral palsy). Therefore, it would be very advantageous for the gynecologist if he could observe immediately any increase of the carbon dioxide concentration in the infant organism if any difficulties occur during the pregnancy and in the course of the delivery so that the gynecologist could immediately undertake the necessary steps in order to prevent any harmful influence on the brain of the infant.

One such prior art electrode cell assembly that can measure ion concentrations in living tissue, and upon which the present invention is an improvement, is described in U.S. Pat. No. 3,973,555 which is incorporated herein by reference. This electrode cell assembly has a conical or rounded tip which is in itself the ion selective member of the measuring electrode that is introduced into the tissue of a living being by penetrating the skin and being fastened thereto by an anchoring means. The anchoring means may be a spiral or helix which surrounds the conical part of the measuring electrode and pierces the skin. The electrode cell assembly basically comprises a reference electrode incorporated in a housing which is filled with an electrolyte and the housing has at least one membrane which is ion sensitive. The reference electrode is a hollow, hydrophilic tube to one end of which is fastened an ion sensitive membrane made of a Lithium-Barium-Silicate glass of low electrical resistivity. The hydrophilic glass tube is filled with a pH buffer solution of potassium chloride. The tube also has a needle-like, silver-silver chloride reference electrode located axially therein but not touching the ion sensitive membrane and glass wall and has the buffer solution surrounding same. The tube, membrane, buffer solution and electrode comprise the internal reference system. The reference electrode extends from the glass tube at the sealed end opposite the membrane and is connected to the center conductor of a coaxial cable that connects the probe to its affiliated equipment.

The hollow glass tube is fastened to the monitor electrode base unit where it extends from a hollow chamber in one end thereof. Within the chamber is another silver-silver chloride reference electrode. One remaining element is a removable tip which has an opening in one end thereof which is only slightly larger than the diameter of the glass tube of the internal reference system and through which tube the ion selective membrane end extends upon assembly of the removable tip to the probe body. A part of the electrode base is shown in FIG. 1 and the tip is shown in FIG. 2.

To utilize the pH probe all parts thereof are sterilized, the hollow chamber in the base unit is then filled with a viscous saturated potassium chloride solution utilizing a syringe and the removable tip is then assembled to the probe body. Upon assembly of the removable tip to the probe body, by displacement the viscous potassium chloride solution is forced into the annular ring formed between the glass shaft of the internal reference system and the hole in the end of the removable tip through which the glass shaft extends. This creates a thin capillary layer of saturated potassium chloride necessary for the operation of the probe. The thickness of this potassium chloride layer is less than 10 micrometers thick and has an axial length of 2 millimeters.

The finer details concerning this prior art pH probe and its operation are found in the U.S. Pat. No. 3,973,555 previously cited and incorporated herein by reference and in other literature in the field.

One of the problems in the prior art which is solved by the present invention lies in the preparation of the pH probe for use. The hollow shaft to which the ion sensitive member is affixed is made of glass and has a diameter of 1.3 millimeters. The glass shaft is relatively weak and prone to breakage, which breakage occurs too frequently when the removable reference junction is installed on the probe body for use. This breakage occurs due to the extremely small tolerance spacing of less than 20 micrometers overall between the glass shaft and the hole through the end of the removable tip. The present cost of replacing the probe when the glass shaft is broken is in the order of $700.

Another problem in the prior art is in using a syringe to charge the probe prior to use which is inconvenient and time consuming.

In accordance with one aspect of my invention, my novel disposable tip is pre-charged with an internal reference electrolyte saturated with silver chloride and including a salt having an ion common with body or tissue fluids, and a syringe is not required to charge the probe assembly with this solution.

In accordance with another aspect of my invention, I provide a tubular sleeve on my novel disposable, removable probe tip which during installation causes the tip to remain coaxially aligned with the glass shaft to prevent breakage thereof.

My invention will be better understood when reading the following description of the invention in conjunction with the drawing in which.

Figure 1:
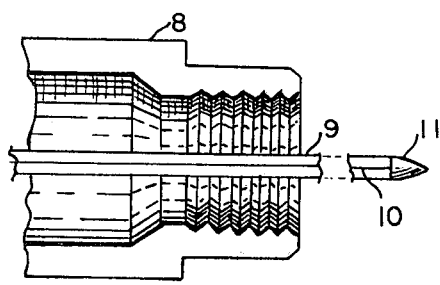
FIG. 1 shows a pH probe base known in the art with which the present invention functions.
Figure 3:
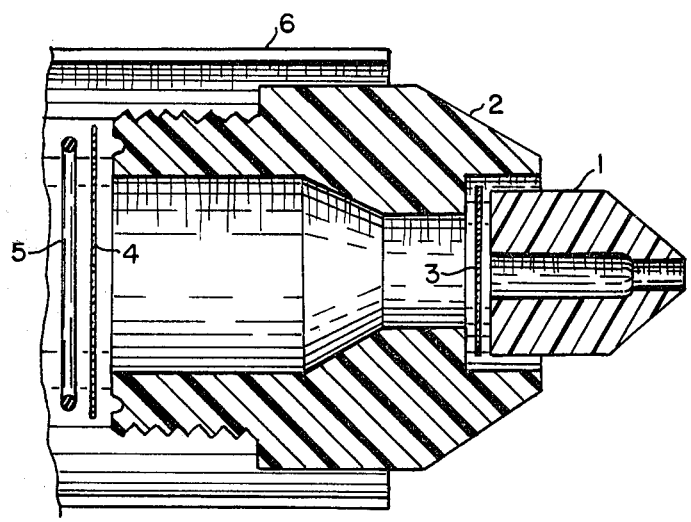
FIG. 3 shows my novel electrolyte precharged disposable tip with installation sleeve.

Referring to FIG. 1, therein is shown the end portion of the prior art pH probe base. The bottom of the cavity within the probe, from which the glass shaft protrudes, is normally lined with a silver-silver chloride reference electrode (not shown) which is electrically connected to the shield conductor of the coaxial cable connecting the probe base to affiliated equipment. To function with my invention the probe base is modified slightly. More particularly, the silver-silver chloride electrode in the bottom of the probe cavity is deleted. In lieu thereof a silver-silver chloride sleeve is placed on the outside of the glass shaft, which silver-silver chloride sleeve is electrically isolated from the silver-silver chloride electrode located inside the glass shaft, but which sleeve is electrically connected to the shield conductor of the coaxial cable connecting the probe to the affiliated equipment. The silver-silver chloride sleeve extends along the outside of the glass shaft not to the end thereof, but rather to be within the internal reference electrolyte saturated with silver chloride and including a salt having a ion common with body or tissue fluids filling the chamber within my novel disposable probe tip when the tip is attached to the probe base as shown in FIG. 3. The silver-silver chloride sleeve provides some structural strength to the glass shaft. To provide additonal structural strength to the glass shaft, the silver-silver chloride layer may be on a stainless steel or other approaporiate metal sleeve and the combination is on the outside of the glass shaft.

Figure 2:
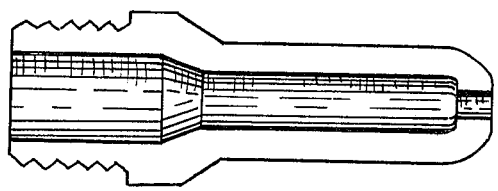
FIG. 2 shows the prior art removable tip that attaches to the prior art probe base shown in FIG. 1.

As seen in FIG. 2 the prior art tip is threaded on the outside to attach to the probe base by screwing into the internal threads of the probe base. My novel disposable probe tip is likewise threaded on its outside and attaches to the probe base by screwing into the internal threads thereof.

FIG. 3 shows the details of my novel disposable, electrolyte precharged probe tip. The tip comprises two molded plastic elements or pieces, 1 and 2, with element 2 being the disposable tip body element which is threaded for screw-on attachment to the probe base. Tip piece 1 has a channel axially therethrough. Spacing is deliberately shown between each of the elements in FIG. 3 to best show the individual elements, which spacing does not really exist in the assembled probe tip.

Tip piece 1 has a small hole through the tip thereof which has the same dimensions as the small hole through the tip of the prior art probe shown in FIG. 2. This hole is very close fitting to the probe glass shaft as previously described and passes therethrough as shown in FIG. 3. In assembly a disc shaped membrane 3 is attached to the base of tip piece 1 to seal the hole therethrough. The combination of tip piece 1 and membrane 3 are then inserted into the opening within the front end of tip body element 2 and is retained therein by either force fit or an adhesive.

The assembly of tip piece 1 with membrane 3 to tip body piece 2 closes off the front end of the internal channel through tip body piece 2. The cavity defined within tip piece 2 by the axial channel therethrough and membrane 3 is filled with the reference electrolyte solution which is then sealed within the cavity by disc shaped membrane 4 which is fastened to the rear of tip piece 2. In this embodiment of the invention tip piece 2 has an annular groove in the bottom thereof, as shown in FIG. 3, which is used as now described to seal the potassium chloride electrolyte within my novel disposable probe tip. After charging the cavity now created within tip body piece 2 with reference electrolyte, a disc shaped membrane is placed over the bottom end of tip piece 2 overlapping the annualar groove in the base therof. Rubber ring 5, having the same diameter as the annular groove in tip piece 2, is then installed by pushing it into the annular groove and capturing membrane 4 within the annular groove at the same time.

It would be obvious to one skilled in the art that rubber ring 5 need not be used to fasten membrane 4 to the base of tip piece 2. In the alternative, other means including an adhesive may be utilized to fasten membrane 4 to the base of tip piece 2 to seal the reference electrolyte therein.

Finally, an installation sleeve 6 having an inside diameter equal to the outside diameter of both tip piece 2 and probe base 8 is affixed to my disposable tip assembly. Installation sleeve 6 coaxially aligns the axis of my disposable tip assembly with the axis of the probe base to assure that the glass shaft of the probe base will pass through the small diameter hole through tip piece 1 without hitting the sides and then very possibly breaking the glass shaft.

Figure 4:
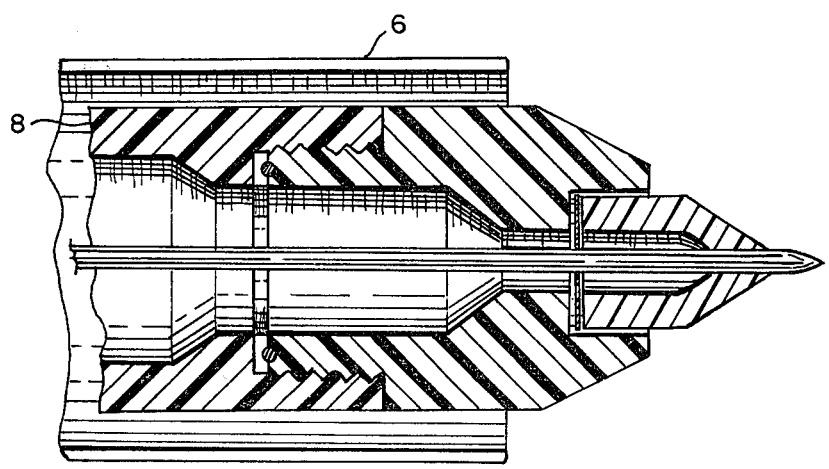
FIG. 4 shows my novel disposable tip attached to the pH probe base.

FIG. 4 shows the assembly of my novel disposable, precharged probe tip affixed to the probe base. It can be seen in FIG. 4 how installation sleeve 6 aligns the axis of both parts as the disposable tip is screwed onto the probe base. During attachment the silver-silver chloride sleeve on the outside of and reinforcing the glass shaft first pierces membrane 4. Membrane 4 is of a meterial that may be punctured but forms a water-tight seal around the puncturing element. Thus, no reference electrolyte is allowed to escape into the cavity area of the probe base. The silver-silver chloride electrode on the outside of the glass shaft is within the reference electrolyte inside the disposable tip to provide electrical connection between the electrolyte and the probe base coaxial cable shield conductor. The tip of the glass shaft next punctures membrane 3 and passes axially through tip piece 1 so that the ion selective tip on the glass shaft just protrudes beyond tip piece 1 when the disposable tip is fully screwed in the probe base as shown in FIG. 4. Membrane 3 is made of a different material than membrane 4 and tears as it is punctured allowing the reference electrolyte within my disposable tip displaced by the glass shaft passing therethrough to flow into the extremely thin spacing between the glass shaft and tip piece 1 as required for the operation of the probe.

As the prior art cavity within probe base 8 serves no function when my invention is used the cavity may be deleted from the base leaving only the area where the threads are within probe base 8.

In an alternative embodiment of my invention, my disposable probe tip may be a single plastic piece rather than the pieces 1 and 3 disclosed herein. There is still a membrane 4 across the rear of the tip piece, but a hand removable plug is interference inserted into the front end to perform the function of the missing membrane 3 which is now deleted. The disposable tip is held in an upright position before the plug is removed by hand and the glass shaft of the probe base is passed through the narrow channel of tip piece 1.

Although two embodiments of my invention have been described herein, such descriptions are intended to be illustrative rather than limiting, and one skilled in the art may think of other embodiments without departing from the spirit and scope thereof as defined in the appended claims.

I claim:

1. A disposable probe tip attachable to an electrode cell to make up a probe assembly used to make a continuous determination of ion concentrations in living tissues wherein the electrode cell has a thin protruding tube and having an ion sensitive membrane on the tip of the tube, the tube having a conductor around the outside thereof but not extending to the membrane, wherein said disposable probe tip comprises:

a housing having a hollow chamber therein and having a first and a second opening communicating with said hollow chamber, an electrolyte solution within the chamber of said housing, first means sealing said first opening, second means sealing said second opening and cooperating with said first sealing means to seal said electrolyte within said chamber, a tip piece with a passage therethrough having a diameter only slightly larger than the diameter of said tube, said tip piece being attached to said housing so as to hold said first sealing means up against said first opening and so that said first and said second openings are coaxial with the axis of said tip piece passage, the tip of said tube first penetrating said second sealing means, then passing through said electrolyte solution, penetrating said first sealing means and then passing through said passage and exiting therefrom as said disposable probe tip is attached to said electrode cell.

2. The invention in accordance with claim 1 wherein said first sealing means comprises a first membrane that allows said electrolyte to very slowly leak through said first membrane around said tube after it has penetrated said first membrane upon said disposable probe tip being attached to said electrode cell to make up said probe assembly, said electrolyte leaking through said first membrane around said tube also passing through said passage around the outside of said tube to contact said living tissues.

3. The invention in accordance with claim 2 wherein said second sealing means comprise a second membrane sealing said second opening of said housing, said second membrane preventing said electrolyte from escaping through said second opening before and after said disposable probe tip is attached to said electrode cell.

4. The invention in accordance with claim 3 further comprising a sleeve partially covering the outside of said housing, said sleeve sliding over the outside of said electrode cell as said disposable probe tip is attached thereto to axially align said tube with said first and said second openings to minimize the chance of breaking said tube as said disposable probe tip is being attached to said electrode cell.

* * * * *